US010918346B2

(12) United States Patent
Nye et al.

(10) Patent No.: US 10,918,346 B2
(45) Date of Patent: *Feb. 16, 2021

(54) VIRTUAL POSITIONING IMAGE FOR USE IN IMAGING (71) Applicant: General Electric Company, Schenectady, NY (US)

(72) Inventors: Katelyn Rose Nye, Glendale, WI (US); John Eric Tkaczyk, Delanson, NY (US); Srikrishnan Viswanathan, Bengaluru (IN); Manu Ramesh, Bengaluru (IN); Nasir Ahmed Desai, Bangalore (IN); Gireesha Chinthamani Rao, Pewaukee, WI (US)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 16/694,433

(22) Filed: Nov. 25, 2019

(65) Prior Publication Data
US 2020/0085385 A1 Mar. 19, 2020

Related U.S. Application Data (63) Continuation-in-part of application No. 15/697,269, filed on Sep. 6, 2017, now Pat. No. 10,568,602.

(51) Int. Cl.
*A61B 6/04* (2006.01)
*A61B 6/00* (2006.01)
*A61B 6/03* (2006.01)

(52) U.S. Cl.
CPC ............. *A61B 6/04* (2013.01); *A61B 6/032* (2013.01); *A61B 6/461* (2013.01); *A61B 6/487* (2013.01); *A61B 6/488* (2013.01); *A61B 6/5223* (2013.01); *A61B 6/5247* (2013.01); *A61B 6/5294* (2013.01); *A61B 6/542* (2013.01); *A61B 6/587* (2013.01)

(58) Field of Classification Search
CPC ....... A61B 6/04; A61B 6/0407; A61B 6/4283; A61B 6/4405; A61B 6/4452; A61B 6/5294; A61B 6/547; A61B 6/584
See application file for complete search history.

(56) References Cited

U.S. PATENT DOCUMENTS

| 9,589,374 | B1 | 3/2017 | Gao |
| 10,340,046 | B2 | 7/2019 | Baker |
| 10,354,049 | B2 | 7/2019 | Mabotuwana |
| 10,568,602 | B2* | 2/2020 | Tkaczyk ............ A61B 6/04 |

(Continued)

FOREIGN PATENT DOCUMENTS

| CN | 107491630 A | 12/2017 |
| CN | 106897573 B | 4/2018 |

(Continued)

*Primary Examiner* — Mark R Gaworecki (57) ABSTRACT

The present approach relates to the use of augmented or enhanced reality to facilitate positioning of one or more of a patient, X-ray source, or detector during an image acquisition. In certain implementations, sensors and/or cameras provide quantitative information about the position of system components and the patient, which may be used to generate a positioning signal (positioning image audio or textual positioning instructions) based upon reference to a prior patient image.

22 Claims, 6 Drawing Sheets (56) References Cited

U.S. PATENT DOCUMENTS

2003/0095692 A1  5/2003  Mundy
2018/0233233 A1  8/2018  Sharma
2019/0008480 A1  1/2019  Gerard
2019/0027244 A1  1/2019  Wu

FOREIGN PATENT DOCUMENTS

| EP | 3338209 A1 | 6/2018 | |
| EP | 3491625 A1 | 6/2019 | |
| JP | 04310099 A | 11/1992 | |
| WO | WO-2016079047 A1 * | 5/2016 | ............. A61B 6/488 |

* cited by examiner

VIRTUAL POSITIONING IMAGE FOR USE IN IMAGING

CROSS REFERENCE TO RELATED APPLICATIONS

This Application is a continuation-in-part of U.S. patent application Ser. No. 15/697,269, filed Sep. 6, 2017, which application is herein incorporated by reference.

BACKGROUND

The subject matter disclosed herein relates to radiographic imaging, including imaging approaches employing a detector that is not fixed in place.

Digital X-ray imaging systems are becoming increasingly widespread for producing digital data which can be reconstructed into useful radiographic images. In current digital X-ray imaging systems, radiation from a source is directed toward a subject, typically a patient in a medical diagnostic application. A portion of the radiation passes through the patient and impacts a detector that is divided into a matrix of discrete elements, e.g., pixels. The detector elements are read out to generate output signals based upon the quantity or intensity of the radiation impacting each pixel region. The signals may then be processed to generate an image that may be displayed for review.

In certain contexts, a mobile X-ray imaging system may employ a portable detector that is not fixed in position or orientation with respect to the X-ray source. Moreover, in fixed X-ray imaging system i.e., wall mounted and X-ray tables, using the X-ray bucky system, the detectors are adjustable and can slide in or out of the system. In such contexts, a technician may manually position the patient and/or portable detector based on an estimation of the geometry of the X-ray source, anatomy to be imaged, and the detector. However, such manual approaches may be inadequate, leading to images that are not of the desired quality and/or of the prescribed anatomy, which may in turn lead to additional images being acquired.

BRIEF DESCRIPTION

In one embodiment, a method for generating a positioning signal is provided. The method includes determining a source/patient (S/P) relative position and a detector/patient (D/P) relative position for a current X-ray system geometry. The method further includes determining a projected area on a detector plane of a detector based on the S/P relative position and the D/P relative position. A prior image of a patient under examination is obtained from a library of prior images and the prior image is registered to the patient based on the projected area on the detector plane. The method also includes generating the positioning signal corresponding to the prior image on a representation of the patient.

In another embodiment, a method for imaging a patient is provided. The method includes positioning a detector relative to an anatomy of interest, such that the anatomy of interest is between an X-ray source and the detector. The method also includes viewing a positioning image on a display, wherein the positioning image depicts a virtual fluoroscopic view based on the relative position of the detector and source to the patient. The positioning image is derived from a prior image of the patient. The method further includes adjusting one or more of the source, the detector, or the patient until the positioning image corresponds to an image to be acquired; and acquiring the image.

In yet another embodiment, an X-ray imaging system is provided. The X-ray imaging system includes an X-ray source, a first camera positioned to correspond to the direction of X-ray emission by the X-ray source and a detector configured to generate signals corresponding to X-ray intensity when exposed to X-ray emission by the X-ray source, the detector comprising one or both of a second camera or sensors. The X-ray imaging system also includes a display and one or more processing circuits. The one or more processing circuits are configured to determine a source/patient (S/P) relative position and a detector/patient (D/P) relative position for the current X-ray imaging system geometry. Based on the S/P relative position and D/P relative position, a projected area on a detector plane of the detector is detected. The one or more processing circuits are configured to obtain a prior image of a patient under examination from a library of prior images and register the prior image to the patient based on the projected area on the detector plane. A positioning signal corresponding to the prior image is then generated.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present embodiments, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

The present approach addresses certain problems associated with positioning a source, patient and detector in an X-ray imaging context. By way of example, in certain contexts portable detectors may be employed with mobile X-ray imaging systems, which may be transported to different patient locations and positioned with respect to a patient. Such mobile imaging approaches are in contrast to conventional fixed or dedicated imaging room contexts. In such fixed or dedicated room contexts the position of the X-ray source and detector may be fixed geometrically (i.e., in terms of position and orientation) with respect to one another or otherwise of known or fixed geometry in a given imaging acquisition.

In contrast, in a mobile X-ray imaging context, the detector may be freely movable and positionable with respect to the X-ray emission source and the patient. By way of example, the detector may be a portable detector that is structurally unconnected to any other component of the imaging system or may be connected by a tether (e.g., cable) that provides a full range of motion up to the length of the tether. However, it should be noted that the present technique may also be employed in fixed X-ray imaging system i.e., wall mounted and X-ray tables using an X-ray bucky system where the detectors are adjustable and can slide in or out of the system.

In conventional X-ray imaging approaches, a light box polygon with cross-hairs is projected onto the patient to facilitate aiming and alignment. This lightbox represents the predicted intersection of the collimator-cone of X-ray stream onto the patient. The operator estimates the anatomical coverage of this cone within the patient to guess where the intended anatomy will project onto the detector. To reduce dose, the operator may use as small an illuminated field size as possible. However, a small field size requires better accuracy on the positioning of the light box and projected anatomy onto the detector. The human judgments involved in this estimation are subject to lack of experience and fatigue, and are thus subject to error, which may lead to re-imaging of the patient of poor quality images on which a diagnosis may be based. Further, following imaging there is no record of the positioning retained except for the x-ray image itself, which is only a two-dimensional (2D) projection, and thus a poor indication of three-dimensional (3D) pose. Therefore, no long term learning can be integrated into the process of accurately estimating the alignment.

In accordance with approaches discussed herein, higher examination throughput, lower dose and lower retake rate in an X-ray imaging context, mobile or otherwise, may be achieved. In accordance with certain aspects, this is achieved by integrating enhanced or augmented reality into the X-ray system workflow. In one implementation, a library of prior radiological images of patients is built and updated, during the previous scans of various patients taken by the given imaging system and others like it at any other locations previously. Registration of the prior radiological image of a particular patient to the patient body at present time during the scan is then calculated in an imaging X-ray system where some or all of the tube focal spot, collimator cone, patient and detector orientation (e.g., roll, pitch, and azimuth) and position (e.g., x, y, and z coordinates or other spatial determinants) are determined.

In one example, one or more cameras and/or proximity sensors are integrated with a portable detector so that the detector-patient relative positioning is determinable. Similarly, the tube/collimator positioning relative to the patient (e.g., the source-patient relative position) is determinable, such as by analysis of camera images. Based on the detector-patient relative positioning and the source/patient relative positioning the collimated cone projection with respect to the detector plane is calculated, thereby defining a "projected area" on the detector plane. This alignment process may be supplemented by one or more low exposure images (e.g., scout or positioning images) being performed prior to main image acquisition. Use of such low exposure images may facilitate protocol optimization (by providing anatomy or patient thickness data to allow energy optimization (e.g., spectrum and/or dose selection) during diagnostic imaging) and position verification.

In one implementation, a prior radiological image of the same patient from the radiological images library is fit to the present patient image. The prior radiological images may include a prior X-ray image, a prior computer tomography (CT) scout, a prior CT/magnetic resonance (MR) coronal slice for a posterioranterior (PA) or anteriorposterior (AP) or sagittal slice view of the patient. The prior radiological image is used to generate a positioning signal. The positioning signal includes a positioning image, such as a "virtual fluoroscopic" image (i.e., digitally simulated fluoroscopic image) corresponding to the projected area. The positioning signal may also include audio or textual positioning instructions. For example, the audio or textual positioning instructions may instruct the patient to move to the left/right by certain distance or rotate their shoulder laterally or may instruct the technician to move the X-ray tube in a particular direction etc. Repeated updates to the positioning signal can follow changes in the patient positioning relative to the source and detector. One or more virtual fluoroscopic images may then be displayed to the system operator to facilitate the alignment of the system prior to primary or diagnostic image acquisition, thereby facilitating and reducing error with respect to positioning the anatomy of interest into the final X-ray image. In one embodiment, the operator has manual control of the X-ray tube head and can reposition/rotate the X-ray tube head to achieve the desired "virtual fluoroscopic" image. Similarly, the operator may also reposition or reorient one or more of the patient or a detector based on the virtual fluoroscopic image to align the system for capture the desired diagnostic image. In certain embodiments, further checks may be performed and changes to the display made to warn of poor performance and undesirable conditions: e.g., too thick a patient that might lead to high noise image, lead-apron not being installed to block sensitive organs from X-rays, a laterality marker being on the wrong side of the patient, the wrong anatomical part or region being in the field of view, and so forth.

In addition, as discussed herein, additional optimizations of the image acquisition protocol and/or image processing may be performed based on the presently described processes that use a patient model generated based on the library of prior patient radiological images. By way of example, in certain aspects, a generalized patient habitus (e.g., a 3D digital twin or representation) is constructed from the sensor-metadata. Following the acquisition, this digital representation may be incorporated into the image data record, for example, through the DICOM header special fields. Improved dose information, such as organ dose, may be calculated from this digital representation by leveraging the three-dimensional (3D) patient positioning and anatomical information. In such approaches, an improved image processing result may be achieved because parameters specific to the digital representation (i.e., the digital twin) may be utilized without the user involvement of estimating and then entering patient-specific parameters into the system digital controls. Further, when the image is retrieved from the PACs and displayed for image review, the metadata, such as the image of the patient position relative to the detector, may be available for reference.

Figure 1:
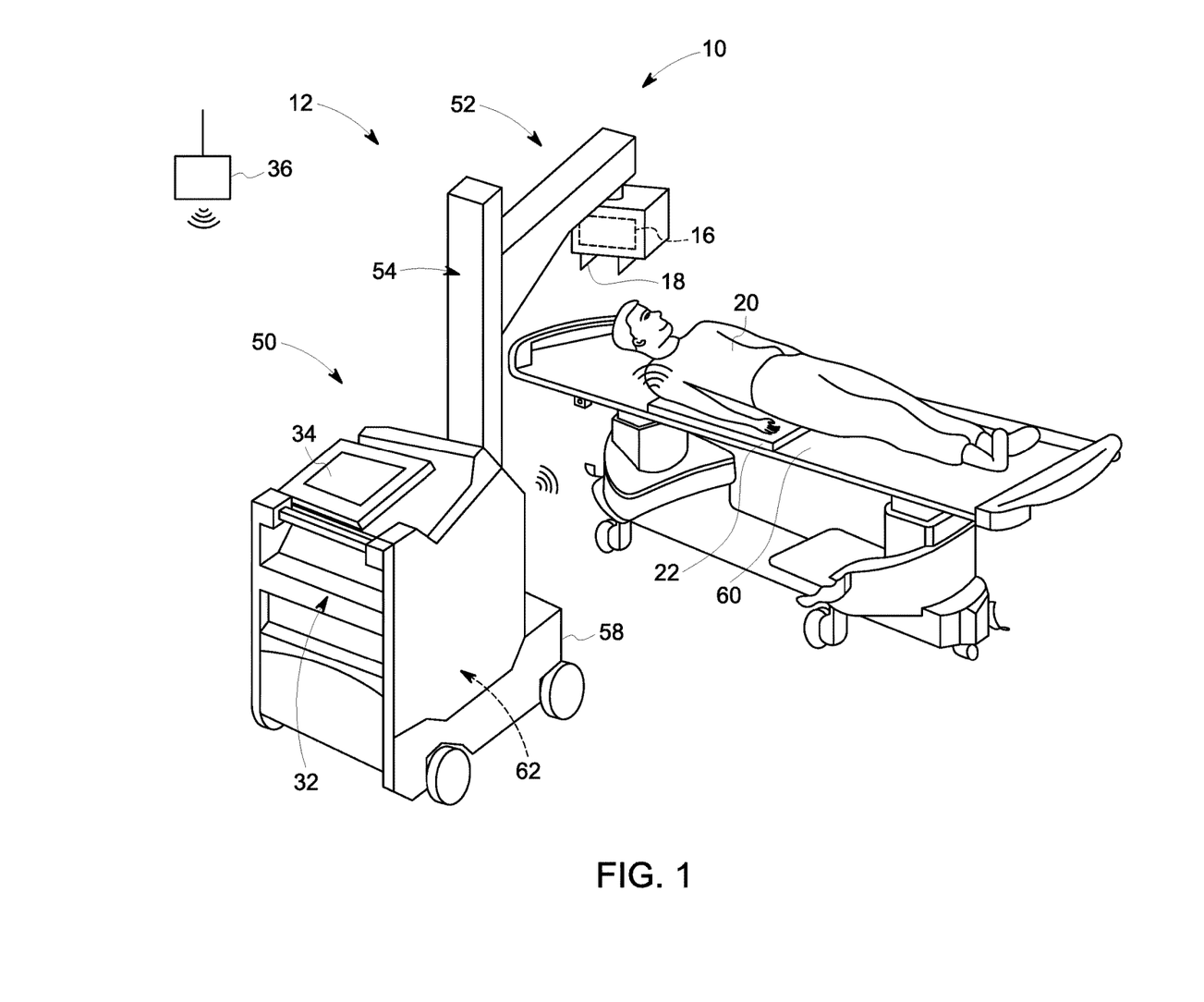
FIG. 1 is perspective view of an embodiment of a mobile X-ray system, equipped in accordance with aspects of the present approach.

With the preceding discussion of the present approach in mind, FIG. 1 depicts an imaging system that may be suitable for implementation of the present approach. In particular an X-ray system is represented and referenced generally by reference numeral 10. In the illustrated embodiment, the X-ray system 10 is a digital X-ray system. The depicted X-ray system 10 is designed both to acquire original image data and to process image data for display in accordance with present techniques. The X-ray system 10 may be a radiographic imaging system used to collect a standalone image, a fluoroscopic imaging system used to collect multiple frames of real-time image data, a tomographic imaging system configured to image a patient region from multiple angles so as to generate a three-dimensional representation, or another suitable type of X-ray based imaging system.

In the embodiment illustrated in FIG. 1, the X-ray system 10 is a mobile imaging system 12 that may be moved to a patient recovery room, an emergency room, a surgical room, a neonatal ward, or any other space to enable imaging of a patient 20 without transporting the patient 20 to a dedicated (i.e., fixed) X-ray imaging room. However, it should be appreciated that aspects of the present approach may also be used in fixed X-ray system environments. However, for the purpose of illustrating the present approach and to provide a real-world context, the present examples primarily focus on mobile X-ray imaging systems employing portable detectors, where certain aspects of the present approach may be particularly useful. In the depicted example, the X-ray system 10 includes a mobile imager or mobile X-ray base station 50 and a portable digital X-ray detector 22 that is freely positionable with respect to the base station 50. In the depicted example, an X-ray base station 50 of the mobile imaging system 12 has a wheeled base 58 to facilitate movement of the station 50.

In the depicted example, a support arm 52 is provided in conjunction with a support column 54 to facilitate positioning of a radiation source 16 and collimator 18 with respect to the patient 20. By way of example, one or both of the support arm 52 and support column 54 may be configured to allow rotation of the radiation source 16 about one or more axes. However, in other examples as discussed herein, the structural and geometric components related to positioning of the X-ray source 16 may vary and/or may provide a different range of configurable motion and orientation of the X-ray source 16. The X-ray source 16 may be provided as an X-ray tube and may be provided in conjunction with a collimator 18 that helps shape or limit the X-ray beam incident on the patient 20.

In a mobile imaging context, as discussed herein, the patient 20 may be located on a bed 60 (or gurney, table or any other support) between the X-ray source 16 and the portable detector 22 and subjected to X-rays that pass through the patient 20. During an imaging sequence, the detector 22 receives X-rays that pass through the patient 20 and transmits imaging data to the base station 50. The portable detector 22 in this example is in wireless communication with the base unit 50, though in other examples communication may be completely or partially via a tethered (i.e., cable) connection. The base station 50 houses electronic circuitry 62 that acquires readout signals from the detector 22 and that may be processed to generate diagnostically useful images. In addition, the electronic circuitry 62 may provide and/or control power to one or both of the X-ray source 16 (i.e., controlling activation and operation of the source 16) and the wheeled base 58 (i.e., a movement system). In the depicted example, the base station 50 also has an operator workstation 32 and display 34 that facilitates user operation of the X-ray system 10. The operator workstation 32 may include a user interface to facilitate operation of the X-ray source 16 and detector 22. In one embodiment, the workstation 32 may be configured to function communicate on or through a network 36 of the medical facility, such as HIS, RIS, and/or PACS. In certain embodiments, the workstation 32 and/or detector 22 may wirelessly communicate with the network 36 wherein data transfer and data processing occur.

Figure 2:
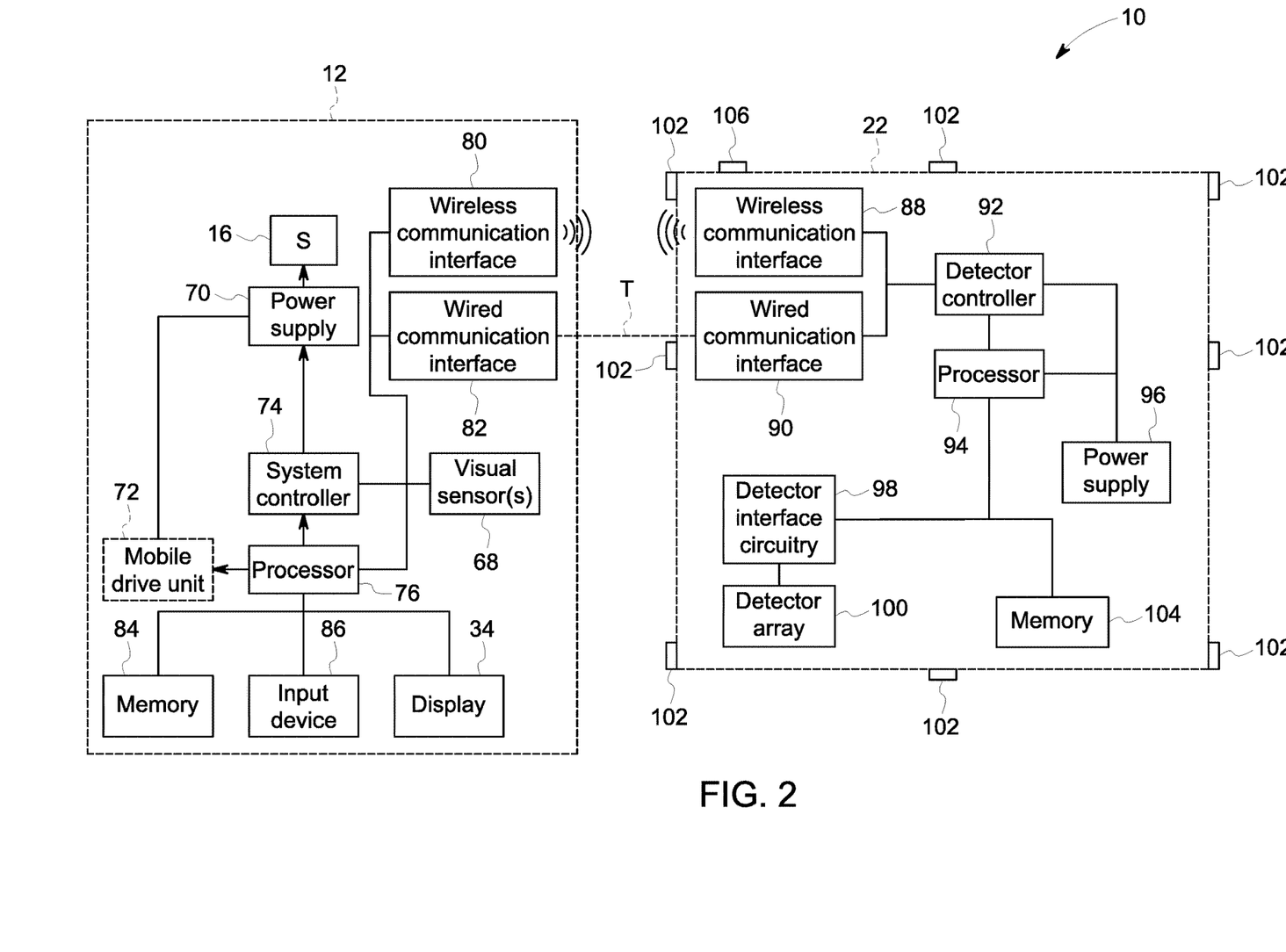
FIG. 2 is a diagrammatical overview of components of an embodiment of an X-ray system in accordance with aspects of the present approach.

While FIG. 1 illustrates schematically aspects of the operation of a mobile X-ray imaging system 10, FIG. 2 diagrammatically illustrates certain components of such a system and their interrelationship. It should also be noted that although, the technique herein is presented with respect to a mobile X-ray imaging system, the present technique may also be employed in fixed X-ray imaging system i.e., wall mounted and X-ray tables using an X-ray bucky system where the detectors are adjustable and can slide in or out of the system.

In the depicted example of FIG. 2, the imager system 12 includes the X-ray source 16 connected to a power supply 70 that furnishes both power and control signals for examination sequences. In addition, in mobile imaging systems the power supply 70 may furnish power to a mobile drive unit 72 of the wheeled base 58. The power supply 70 is responsive to signals from a system controller 74. In general, the system controller 74 commands operation of the imaging system to execute examination protocols and to process acquired image data. In the present context, the system controller 74 also includes signal processing circuitry, typically based upon a general purpose or application-specific circuitry, associated memory circuitry for storing programs and routines executed by the computer, as well as configuration parameters and image data, interface circuits, and so forth. The system controller 74 may include or may be responsive to a processor 76. The processor 76 receives image data from the detector 22 and processes the data to reconstruct an image of a subject. In addition, the processor 76 may generate, as discussed herein, a positioning signal which may include a positioning image, such as a virtual fluoroscopic image for use in aligning the system for an image acquisition or audio/textual positioning instructions. For example, the audio or textual positioning instructions may instruct the patient to move to the left/right by certain distance or rotate their shoulder laterally or may instruct the technician to move the X-ray tube in a particular direction etc. With this in mind, the processor 76, in accordance with the present approach may receive inputs from sensor(s) 102 (e.g., position and/or orientation sensors, proximity sensors, and so forth) and/or a camera 106 on the detector 22 or from one or more visual sensor(s) 68 (e.g., cameras) of the imager system 12 to provide enhanced or augmented positioning of the detector 22 in an examination setting, such as by virtual or augmented reality presentation.

In the implementation shown, the processor 76 is linked to a wireless communication interface 80 that allows wireless communication with the detector 22, e.g., a portable detector. Further, the processor 76 may be linked to a wired communication interface 82 that allows communication with the detector 22 via a tether (e.g., a multi-conductor cable). The imager system 12 may also be in communication with a server. The processor 76 is also linked to a memory 84, an input device 86, and the display 34. The memory 84 stores configuration parameters, calibration files received from the detector 22, and lookup tables used for image data processing. The input device 86 may include a mouse, keyboard, or any other device for receiving user input, as well as to acquire images using the imager system 12. The display 34 allows visualization of output system parameters, images, and so forth.

The detector 22 includes a wireless communication interface 88 for wireless communication with the imager system 12, as well as a wired communication interface 90, for communicating with the detector 22 when it is tethered to the imager system 12. The detector 22 may also be in communication with a server. It is noted that the wireless communication interface 88 may utilize any suitable wireless communication protocol, such as an ultra wideband (UWB) communication standard, a Bluetooth communication standard, or an 802.11 communication standard, or any other suitable wireless communication standard. Moreover, the detector 22 is coupled or includes a detector controller 92 which coordinates the control of the various detector functions. For example, the detector controller 92 may execute various signal processing and filtration functions, such as for initial adjustment of dynamic ranges, interleaving of digital image data, and so forth. The detector controller 92 is responsive to signals from the system controller 74, as well as the detection circuitry 78. The detector controller 92 is linked to a processor 94 that in turn is linked to a memory 104. The processor 94, the detector controller 92, and all of the circuitry receive power from a power supply 96. The power supply 96 may include a battery. In some embodiments, the detector 22, including the power supply 96, may receive power from the power supply 70 when tethered to the imager system 12.

In the depicted example the processor 94 is linked to detector interface circuitry 98. In one embodiment, the detector 22, which may be used in radiographic, fluoroscopic, tomographic, or other imaging operations, converts X-ray photons incident on its surface to lower energy (e.g., optical light) photons. The detector 22 includes a detector array 100 that includes an array of photodetector elements that generate responsive electrical signals in response to the light photons generated in this manner such that the electrical signals are representative of the number of photons or the intensity of radiation impacting individual pixel regions of the detector surface. Alternatively, the detector 22 may convert the X-ray photons directly to electrical signals (i.e., a direct conversion type detection mechanism). These electrical signals are converted to digital values by the detector interface circuitry 98, which provides the values to the processor 94 to be converted to imaging data and sent to the imager system 12 to reconstruct an image of the features within a subject. Alternatively, the imaging data may be sent from the detector 22 to a server to process the imaging data.

In the depicted example, processor 94 and communication interfaces 88, 90 are further linked to one or more position and/or orientation sensors that may be provided in one or various locations on the portable detector 22. The sensors 102 may include, but are not limited to proximity sensors employing electrical capacitance or inductance, acoustic impedance and reflection, and so forth. In accordance with the present approach the position and/or orientation sensors may provide spatial localization data for one or more regions of the detector with respect to the patient 20 (e.g., x, y, z—coordinates, polar coordinates, or other reference frame data) and/or may provide orientation data (e.g., roll, pitch, azimuth) with respect to the patient 20. By way of example, the sensors 102 may be proximity sensors positioned around the perimeter of the detector 22 which sense proximity of the patient body to each sensor 102, such as via electrical capacitance or inductance in the near-field limit (e.g., using small feature plates and coils), via acoustic impedance and reflection, and so forth.

With the preceding discussion of an imaging system 10 in mind, in accordance with the present approach a portable detector 22 is positioned and oriented with respect to a patient anatomy of interest and an X-ray emission source 16 of a mobile system X-ray imager 12, allowing augmented reality feedback to be provided to the operator. Aspects of this approach are depicted graphically in FIG. 3. For example, turning to FIG. 3, a patient 20 is depicted in a semi-reclining position on a bed 60. As part of an imaging procedure, the patient 20 is exposed to an X-ray beam corresponding to an X-ray exposure field 154 that projects from the X-ray source 16 to a detector 22 such that a region of the patient 20 to be imaged is between the X-ray source 16 and detector 22. A collimator 18 (FIG. 1) associated with the source 16 of X-ray emission may be adjusted (manually or automatically) to shape the X-ray beam incidence on the patient 20. An X-ray blocking cover or apron 156 may be positioned on parts of the patient that are not part of the examination.

Figure 3:
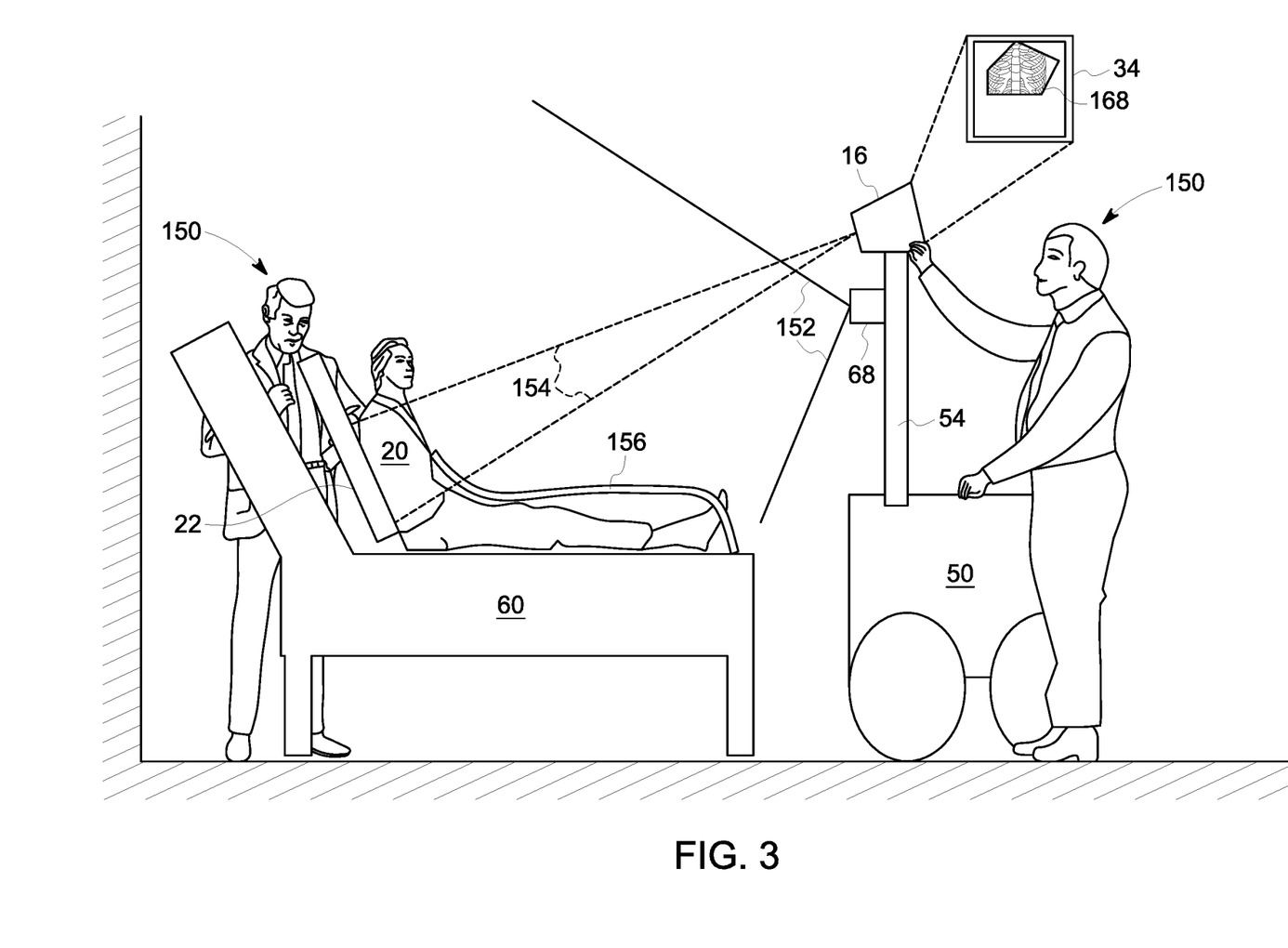
FIG. 3 illustrates schematically aspects of patient and/or detector positioning in accordance with aspects of the present approach.

In one implementation of the present approach, a visual sensor 68 in the form of a camera is positioned in an elevated location on the X-ray base station 50, such as on support column 54. In one embodiment, the camera is capable of stereovision and generates corresponding stereoscopic visual data that provides the distance from the camera. The field of view of the visual sensor (e.g., camera) spans a solid angle 152 including the patient 20, detector 22 and the operator 150.

In the depicted example, the detector 22 is a portable detector capable of being freely moved and positioned with respect to the X-ray base station 50. In this example, the detector 22 has been placed between the patient 20 and the bed 60 by an operator 150. A light box polygon may be projected onto the patient 20 to facilitate positioning of the patient 20 and/or detector 22 in setting up an image acquisition. As discussed herein, to facilitate positioning the detector 22, the operator 150 inspects a visual/audio/textual indication in the form of a positioning signal, such as a virtual fluoroscopic image, that conveys an estimation of the image that would be acquired based on the current detector, patient, and X-ray source geometric alignment (e.g., the position (x, y, z) and orientation (roll γ, pitch β, azimuth α) for each of the detector plane, X-ray emission spot, and imaged region of the patient). The positioning signal may be reviewed and updated in real-time to facilitate positioning of the detector, patient, and X-ray source by one or more operators to acquire the prescribed image(s) with non-diagnostic imaging energy or reduced dose exposure to the patient. In certain implementations, other visual, haptic or auditory aids, such as a color-coded (e.g., red/green) acceptance indicator and/or laterality (left/right) indicators may also be displayed to facilitate the image acquisition process.

In the depicted example, an operator 150 (who may be the same operator that positions the detector 22 or a different operator) is shown aligning the X-ray exposure field 154 relative to the detector 22 by articulation of the X-ray source 16 mounted to a system support 110 by means of some combination of manual adjustment (e.g., manually tilting or aiming the X-ray source 16) or by electronic controlled adjustment (e.g., an automated source adjustment control, such as may be operated by a button, slider, joy-stick or switch). As shown, one or more of these adjustments may be in conjunction with reviewing a positioning signal, such as a virtual fluoroscopic image 168, displayed to the operator(s) or audio/textual positioning instructions updated in real-time to show current alignment. As shown in FIG. 3, the virtual fluoroscopic image 168 may reflect the collimation performed on the X-ray beam to limit exposure to only the anatomy of interest, and may thus may correspond to an irregular shape (here an irregular pentagon) defining or outline a limited aspect of the patient anatomy.

Figure 4:
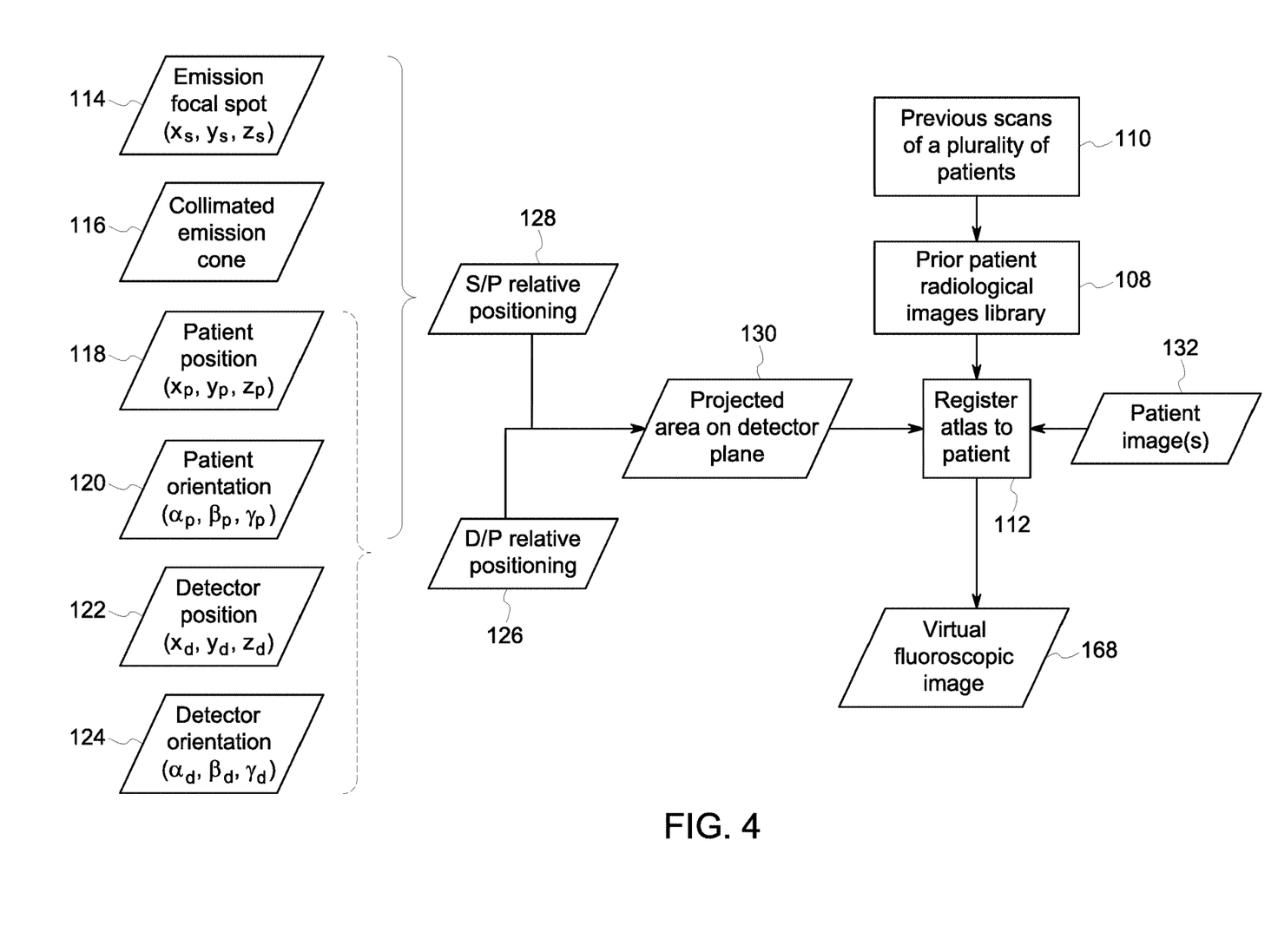
FIG. 4 is a flowchart depicted steps in the generation of a virtual fluoroscopic image, in accordance with aspects of the present approach.

Turning briefly to FIG. 4, a block diagram illustrating aspects of generating the virtual fluoroscopic image 168 is shown. As may be appreciated, the depicted approach may be understood in the context of various features and structures of the imaging system, including detector 22, discussed herein.

In the depicted example, a library 108 of prior radiological images of the patient is used in the generation of a virtual fluoroscopic image 168 which may be displayed and updated in real-time as a positioning image. In one embodiment, the library 108 of prior radiological images comprises prior X-ray image data (e.g., cross-sectional view, 3D models, planar views, annotated or identified anomalies, and so forth) of a plurality of patients. Apart from X-ray image data, the prior radiological images may include, a prior computer tomography (CT) scout, a prior CT/magnetic resonance (MR) coronal slice for a posterioranterior (PA) or anterior-posterior (AP) or sagittal slice view of the patient. The prior radiological image data can be categorized or characterized by multiple definable patient parameters. The multiple definable patient parameters include patient first name, patient last name, patient date of birth, patient identification number (ID), patient gender, age, body mass index, anatomic region of interest, a specific view of the anatomic region of interest, imaging or modality examination type (X-ray, CT, Mill machines etc.), date range for the examination, machine identification, examination department, reason for the examination and so forth. The library 108 of prior radiological images may be constructed and updated using previous scan images of the plurality of patients. Such previous scans may be employed during operation of the imaging system 10 and/or of comparable systems to provide to update the library 108 of prior radiological images over time.

Figure 5:
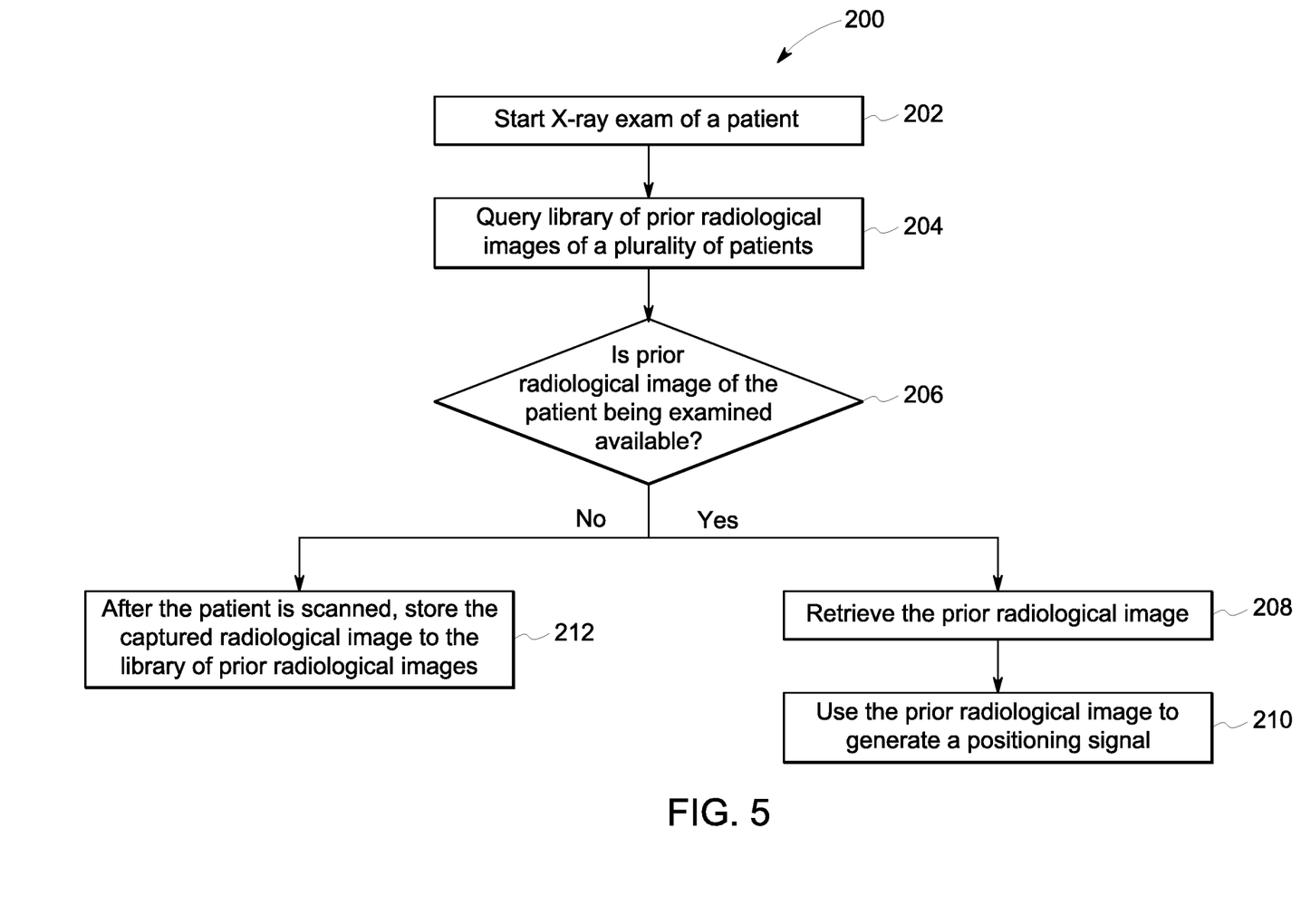
FIG. 5 is a flowchart depicted steps in the utilization of prior radiological images for examining a patient, in accordance with aspects of the present approach.

FIG. 5 shows a flowchart 200 of a method for utilizing the library of prior radiological images for examining a patient. At step 202, the method includes starting the X-ray Exam of a patient. This step may include entering or retrieving the patient details such as name, patient ID, anatomic region of interest or a specific view of the anatomic region of interest etc. at the base station 50. At the next step 204, the entered patient details are used to query the library of prior radiological images of the plurality of patients. At step 206, it is determined whether any prior radiological image of the patient being examined is available or not in the library. If any such prior radiological image of the patient being examined is available, then that prior image is retrieved at step 208. Finally, at step 210, the retrieved prior radiological image is used to generate a positioning signal which is then further used to position the detector or patient to scan the region of interest of the patient. However, if the prior radiological image of the patient being examined is not available at step 206, then examination of the patient is continued with the expertise of the operator and once the patient is examined, the captured X-ray image is then stored into the library of prior radiological images at step 212 in order to update the library.

Turning back to FIG. 4, registration (step 112) of the prior patient radiological image to the patient 20 is calculated based on a model of the X-ray system that reflects the known position 114 of the focal spot 114 of the X-ray source 16 ($x_s$, $y_s$, $z_s$), the collimated X-ray emission cone 116, patient position ($x_p$, $y_p$, $z_p$) 118, patient orientation ($\alpha_p$, $\beta_p$, $\gamma_p$) 120, detector position ($x_d$, $y_d$, $z_d$) 122, and detector orientation ($\alpha_d$, $\beta_d$, $\gamma_d$) 124. In the registration step 112, a representative view which is a modification of the prior image may be fitted to a view of the patient (such as a current camera view or a stylized representation) based on the present geometry of the detector 22, patient 20, and source 16 (e.g., X-ray tube and collimator 18). In one embodiment, the modification of the prior image includes magnification, reduction, enhancement or rotation of the prior image to fit the image onto the region of interest of the patient body. In particular, the patient and detector position and orientation information, 118, 120, 122, 124 may be used to determine the detector/patient relative positioning 126 while the source and patient position and orientation information, 114, 116, 118, 120 may be used to determine the source/patient relative positioning 128, which may be used to derive a geometric model of the X-ray system as currently positioned. In this manner, the detector/patient relative positioning 126 and source/patient relative positioning 128 can be used to derive the source/detector relative positioning. The two-step process of acquiring detector/patient relative positioning 126 and source/patient relative positioning 128 allows source/detector relative positioning to be determined even when the detector is not visible from the source 16 (or a camera mounted near the source 16), allowing the detector position and orientation to be determined relative to the source 16 even when the detector 22 is behind the patient 20.

The detector/patient relative positioning 126 may be derived, in one implementation, using sensors 102 (e.g., proximity sensors) provided on the detector 22 and/or using camera 106 provided on the detector 22. The source/patient relative positioning 128 may be derived from analysis of camera images, such as may be captured by a stereo, depth camera provided as a visual sensor 68 on the imager 12. In addition to or instead of using data derived from the sensors 102, position and orientation 122, 124 of the detector 22 may be determined relative to a patient body part by detecting changes that occur during the insertion of the detector 22 under the patient 20. For example, the starting position of a detector 22 may be visible to a system camera 68 initially. The detector position 122 may be tracked as the detector 22 is slid under the patient 20. Proximity sensors 102 may be employed during this insertion process as they engage with the changing near-field impedance environment caused by the anatomy of the body part.

The source/patient relative position 128 and detector/patient relative position 126, may be used to derive the collimated X-ray cone projection (i.e., the projected area 130) of the X-ray emission onto the plane of the detector 22. The registration process 112 may be supplemented or facilitated by one or more low exposure images 132, such as one or more scout images acquired by the imaging system 10. As shown in FIG. 4, based on the registration or fitting of the relevant prior patient radiological image to the patient (e.g., low exposure patient image 132), a positioning image, such as a virtual fluoroscopic image 168, is generated from the prior patient radiological image that corresponds to the projected area 130.

Turning back to FIG. 3, the positioning image (and/or the acceptance indicator and laterality markers) may be displayed on a display device 34 that, in one implementation, is provided on the base station 50, such as on the back of the source 16. In this context, the positioning image (here a virtual fluoroscopic image 168) may be observed by the operator(s) 106 to facilitate adjustment of one or more of the source 16, patient 20, and/or detector 22, with the positioning image being updated in response to adjustments to one or more of these factors. As may be appreciated in other implementations the positioning image may be displayed on the imaging console of the base station so as to be visible to an operator positioning and/or orienting one or more of the source 16, patient 20, or detector 22. More generally, the display 34 may be provided in any suitable context that allows the operator 150 to view the positioning image including, but not limited to, displays provided as part of the imaging system 10, portable electronic devices or computers configured to communicate with the imaging system 10 (e.g., tablet computers, laptop computers, virtual reality goggles or glasses, augmented reality goggles or glasses, cellular telephones, and so forth), or monitor or workstations provided in the same room, but separate from the imaging system 10.

In such approaches, the operator(s) 150 adjusts the position or orientation of the source 16, patient 20, and/or detector 22 to achieve a configuration where the target anatomy is represented and suitable positioned (e.g., centered) in the positioning image shown on display 34. During adjustment of the source 16, the collimated exposure field 154 is adjusted automatically by the system to illuminate only the detector area 22, such as based on the position and orientation data received form the detector 22 and/or based on the camera inputs generated at the base station 50.

Figure 6:
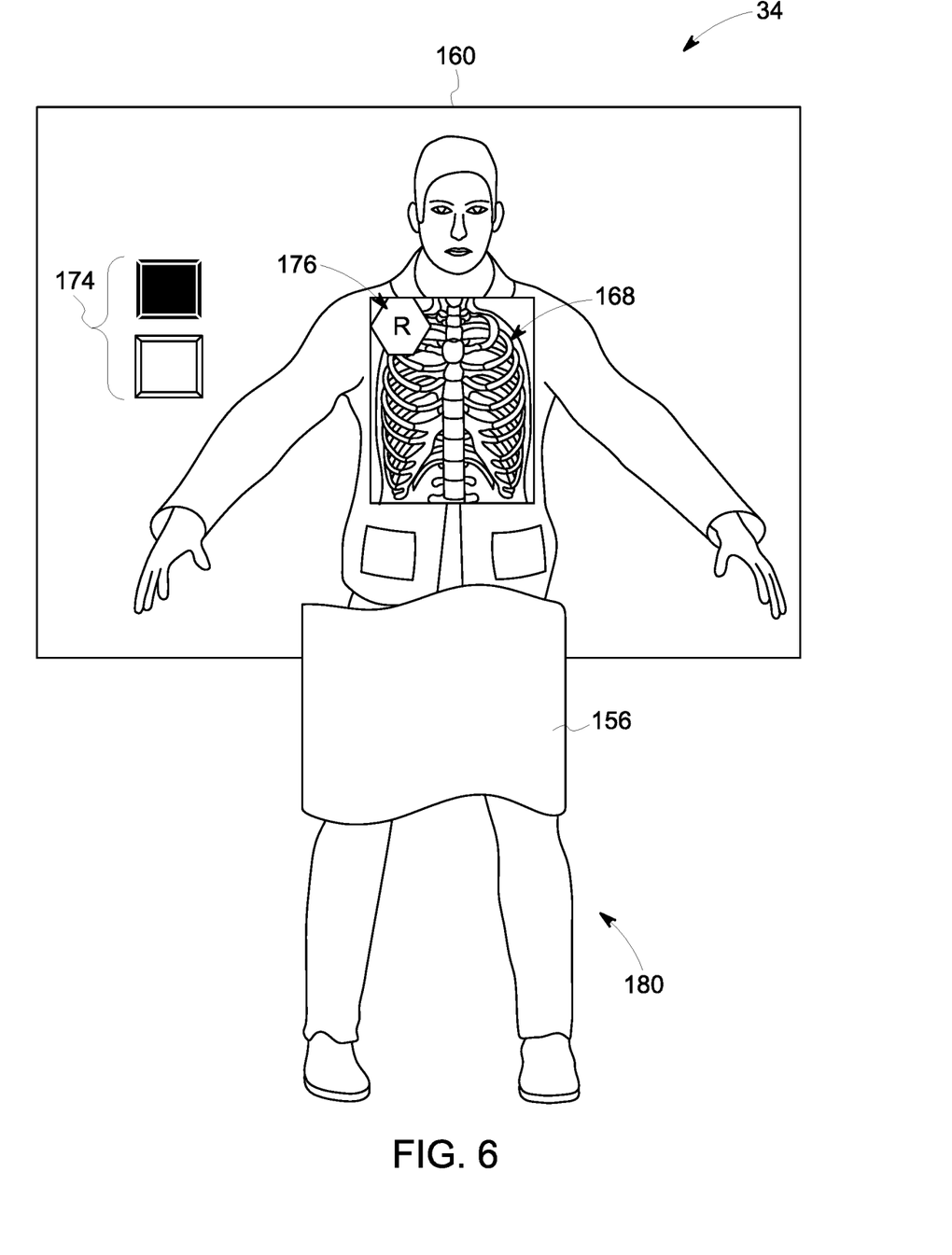
FIG. 6 schematically illustrates a virtual fluoroscopy image fitted to a patient representation in accordance with aspects of the present approach.

By way of further example, and turning to FIG. 6, a diagrammatic view of the superimposition of a virtual fluoroscopic view on a patient representation or image is depicted in accordance with implementations of the present approach. The patient representation may be a realistic representation (e.g., an image generated by a camera 68) or a pseudo-realistic or stylized representation, which may be generated or selected based on patient parameters such as height, weight, body mass index, gender, and so forth. In certain embodiments a camera image, if used, may be degraded and stylized for display so that no personal information readily available. In particular the face and identifying marks are not displayed in such implementations. Such image degradation may be built into the camera chip. In certain embodiments the camera privacy function is verified by one or more parties and only verified cameras will work with the system due to a public/private key-based password being employed.

By way of example, FIG. 6 depicts a visual representation 180 of a patient 20. As discussed herein, all or part of the representation 180 may be displayed in conjunction with the positioning image, e.g., a virtual fluoroscopic image 168, which may overlay or be superimposed on all or part of the representation 180. In the depicted example, a portion of the representation 180 is depicted as being visualized within a frame boundary 160 corresponding to the display screen. By way of example, the portion of the representation 180 visible in the frame boundary 160 (e.g., display window) visible to the operator 150 will generally correspond to what is seen by the camera and will include the portion of the patient 20 on which the X-ray field will be incident during imaging. Thus, by viewing a display 34, the operator 150 can visualize a portion of the patient anatomy that encompasses the anatomic region to be imaged.

In the depicted example, a positioning image, here virtual fluoroscopic image 168, is displayed superimposed over the patient representation 180. The bounds of the superimposed image may be determined based on the settings of the collimator 18 at that time and may correspond to the area over which X-rays would be incident in the event of source activation or may correspond to a broader range of possible exposure area. Based on the superimposed positioning image, the operator 150 may move or re-orient one or more of the X-ray source 16, the patient 20, or the portable detector 22 and/or may adjust the collimator 18 to obtain the desired X-ray view. As discussed herein the positioning image, such as the depicted virtual fluoroscopy image 168, depicts an estimation or approximation (such as drawn from a library 108 of prior radiological images) of an X-ray (e.g., fluoroscopic) image representative of what would be obtained for the current detector-patient relative positioning 126 and source-patient relative positioning 128 and based on one or more patient identification parameters searchable within the library 108 of prior X-ray images.

In addition, other features may be displayed instead of or in addition to the superimposed positioning image. By way of example, an acceptance indicator 174 (e.g., a color-based acceptance indicator) and/or laterality markers 176 (e.g., right (R)/left (L)) may be displayed to facilitate positioning and alignment of the detector 22, patient 20, and source 16. In one such implementation, the acceptance indicator 174 may indicate by its color state whether performance conditions are met, such as whether the patient is too thick for the current emission setting (e.g., energy emission spectrum), which might lead to unacceptable levels of noise in the diagnostic image. Such a determination may be made using a low energy test or scout image, which may also be used to generate one or more anatomic or structural references for the prior radiological image fitting process. The acceptance indicator 174 may also provide an indication as to the presence and/or placement of a lead apron 156 with respect to tissue or organs to be shielded.

Thus, at a glance of the display 34, an operator can ascertain the anatomic expanse on which X-rays will be incident based on the current source, patient, and detector geometry, and the expected or estimated image that would be acquired (i.e., the virtual fluoroscopic view) prior to actually exposing the patient to radiation or after only low-dose exposure (e.g., a scout image). In addition, in implementations employing laterality markers 176 and/or acceptance indicators 174, the orientation of the patient or the acceptability of the present geometry, respectively, may also be ascertained. In this manner, operator error may be reduced, thus reducing image retakes, and unnecessary scatter and radiation dose may be reduced.

In certain implementations, other optimizations to the image acquisition protocol and image processing may be performed based on the above-described process. For example, the patient model generated as part of fitting the prior patient radiological images may be used for additional functions. In one such approach a generalized patient habitus (e.g., a "digital twin") may be generated from the sensor-metadata for each patient. Following the image acquisition, this digital twin may be incorporated into the image data record, such as through the DICOM header special fields. Improved dose information, including organ dose and other X-ray exposure parameters, may be calculated using the digital twin based on the 3D patient positioning and on available anatomical information. In such an approach, an improved image processing result may be achieved because parameters specific to the digital twin may be utilized without the need to estimate and enter patient-specific parameters into the system digital controls.

When the image is retrieved from the PACs and displayed for image review, the metadata, such as the image of the patient position relative to the detector, may be made available for reference. By way of example, the body model (i.e., digital twin) corresponding to a given image acquisition may be provided for viewing along with the corresponding X-ray image during image review to provide landmarks and context to the reviewer. For example, the reviewer may be able to tell by reference to the corresponding body model how the positioning of the patient was carried out.

In addition, it may be noted that the present approach may provide various post-acquisition options. By way of example, once a diagnostic image is acquired, image processing may be performed to enhance specific anatomical regions and with specific frequency/contrast levels to reveal the target diagnostic features. For example, in chest imaging the lungs need to be enhanced, but features such as the spine do not. Similarly, in extremity imaging, high resolution is needed to see the trabecular structure in the bones. Further, in one embodiment, by utilizing prior radiological images, the exact same portion of patient's body can be imaged that was scanned earlier with the exact same parameters of the X-ray system. This helps in making side by side comparisons of the imaging exams i.e., X-ray images and analyze the progression of a disease i.e., whether the condition is improving or worsening. The side by side comparisons of the X-ray images may then be used by artificial intelligence (AI) algorithms to build notification rules.

Technical effects of the invention include the use of augmented or enhanced reality to reduce operator error, leading to fewer retakes of X-ray images on mobile and fixed systems and better image quality at review. In certain implementations, sensors and/or cameras provide quantitative information about the position of system components and the patient, which may be used to generate a positioning signal based upon reference to a prior patient radiological image. Reduction of unnecessary scatter and radiation dose is achieved because a smaller field of view can be used while ensuring the target anatomy is present in the final X-ray image.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for generating a positioning signal, comprising:
   determining a source/patient (S/P) relative position for a current X-ray system geometry;
   determining a detector/patient (D/P) relative position for the current X-ray system geometry;
   based on the S/P relative position and D/P relative position, determining a projected area on a detector plane of a detector;
   obtaining a prior image of a patient under examination from a library of prior images;
   registering the prior image to the patient based on the projected area on the detector plane;
   generating the positioning signal corresponding to the prior image on a representation of the patient; and
   wherein determining the D/P relative position comprises:
      acquiring one or both of camera or sensor data generated at the detector; and
      determining the D/P relative position from one or both of the camera or sensor data.

2. The method of claim 1, wherein the positioning signal comprises a positioning image or audio or textual positioning instructions.

3. The method of claim 1, wherein the library of prior images comprises prior X-ray images, prior computer tomography (CT) scouts, prior CT/magnetic resonance (MR) coronal slice views for a posterioranterior (PA) or anteriorposterior (AP) or sagittal slice views of a plurality of patients.

4. The method of claim 2, wherein the library of prior images is queried based on a plurality of factors to obtain the prior image of the patient under examination.

5. The method of claim 3, wherein the plurality of factors to query the library of prior images include patient first name, patient last name, patient date of birth, patient identification number (ID), patient gender, age, body mass index, anatomic region of interest, a specific view of the anatomic region of interest, imaging or modality examination type, date range for the examination, machine identification, examination department, reason for examination or combinations thereof.

6. The method of claim 1, wherein determining the S/P relative position comprises:
   acquiring one or more images of the patient from a camera positioned on an X-ray system comprising the source; and
   determining the S/P relative position from the one or more images.

7. The method of claim 1, wherein determining the projected area on the detector plane comprises:
   determining a source/detector (S/D) relative position for the current X-ray system geometry based on the source/patient (S/P) relative position and the detector/patient (D/P) relative position; and
   determining the projected area on the detector plane using the S/D relative position.

8. The method of claim 1, wherein the library of prior images is generated based on previous radiological examinations of a plurality of patients.

9. The method of claim 1, wherein the prior image is registered to the patient using one or more images of the patient acquired using a non-diagnostic imaging energy or reduced dose exposure to the patient.

10. The method of claim 1, further comprising:
    displaying one or both of an acceptance indicator or a laterality marker with the positioning signal.

11. The method of claim 1, further comprising:
    updating the positioning signal in response to one or more of the source, the detector, or the patient changing position or orientation.

12. A method for imaging a patient, comprising:
positioning a detector relative to an anatomy of interest, such that the anatomy of interest is between an X-ray source and the detector;
viewing a positioning image on a display, wherein the positioning image depicts a virtual fluoroscopic view based on the relative position of the detector and source to the patient, wherein the positioning image is derived from a prior image of the patient;
adjusting one or more of the source, the detector, or the patient until the positioning image corresponds to an image to be acquired; and
acquiring the image.

13. The method of claim 12, wherein the positioning image is superimposed on a representation of the patient for viewing.

14. The method of claim 12, wherein the prior image is obtained by querying a library of prior images of a plurality of patients based on a plurality of factors.

15. The method of claim 14, wherein the plurality of factors to query the library of prior images include patient first name, patient last name, patient date of birth, patient identification number (ID), patient gender, age, body mass index, anatomic region of interest, a specific view of the anatomic region of interest, imaging or modality examination type, date range for the examination, machine identification, examination department, reason for examination or combinations thereof.

16. The method of claim 12, wherein the virtual fluoroscopic view is derived or selected from the prior image and registered to the patient based on a projected area on the detector plane determined for the current X-ray system geometry.

17. An X-ray imaging system, comprising:
an X-ray source;
a first camera positioned to correspond to the direction of X-ray emission by the X-ray source;
a detector configured to generate signals corresponding to X-ray intensity when exposed to X-ray emission by the X-ray source, the detector comprising one or both of a second camera or sensors;
a display;
one or more processing circuits configured to:
determine a source/patient (S/P) relative position for a current X-ray imaging system geometry;
determine a detector/patient (D/P) relative position for the current X-ray imaging system geometry;
based on the S/P relative position and D/P relative position, determine a projected area on a detector plane of the detector;
obtain a prior image of a patient under examination from a library of prior images;
register the prior image to the patient based on the projected area on the detector plane; and
outputting a positioning signal corresponding to the prior image on a representation of the patient.

18. The X-ray imaging system of claim 17, wherein the S/P relative position is determined from one or more images acquired by the first camera.

19. The X-ray imaging system of claim 17, wherein the D/P relative position is determined from data acquired by one or both of the second camera or sensors.

20. A method for generating a positioning signal, comprising:
determining a source/patient (S/P) relative position for a current X-ray system geometry;
determining a detector/patient (D/P) relative position for the current X-ray system geometry;
based on the S/P relative position and D/P relative position, determining a projected area on a detector plane of a detector;
obtaining a prior image of a patient under examination from a library of prior images;
registering the prior image to the patient based on the projected area on the detector plane;
generating the positioning signal corresponding to the prior image on a representation of the patient; and
wherein the library of prior images comprises prior X-ray images, prior computer tomography (CT) scouts, prior CT/magnetic resonance (MR) coronal slice views for a posterioranterior (PA) or anteriorposterior (AP) or sagittal slice views of a plurality of patients.

21. A method for generating a positioning signal, comprising:
determining a source/patient (S/P) relative position for a current X-ray system geometry;
determining a detector/patient (D/P) relative position for the current X-ray system geometry;
based on the S/P relative position and D/P relative position, determining a projected area on a detector plane of a detector;
obtaining a prior image of a patient under examination from a library of prior images;
registering the prior image to the patient based on the projected area on the detector plane;
generating the positioning signal corresponding to the prior image on a representation of the patient; and
wherein determining the S/P relative position comprises:
acquiring one or more images of the patient from a camera positioned on an X-ray system comprising the source; and
determining the S/P relative position from the one or more images.

22. A method for generating a positioning signal, comprising:
determining a source/patient (S/P) relative position for a current X-ray system geometry;
determining a detector/patient (D/P) relative position for the current X-ray system geometry;
based on the S/P relative position and D/P relative position, determining a projected area on a detector plane of a detector;
obtaining a prior image of a patient under examination from a library of prior images;
registering the prior image to the patient based on the projected area on the detector plane;
generating the positioning signal corresponding to the prior image on a representation of the patient;
wherein the positioning signal comprises a positioning image or audio or textual positioning instructions; and
wherein the library of prior images is queried based on a plurality of factors to obtain the prior image of the patient under examination.

* * * * *